(12) United States Patent
Lichtenstein et al.

(10) Patent No.: US 9,192,468 B2
(45) Date of Patent: Nov. 24, 2015

(54) METHOD FOR ANCHORING A MITRAL VALVE

(71) Applicant: Kardium Inc., Richmond (CA)

(72) Inventors: Samuel Victor Lichtenstein, Vancouver (CA); Daniel Gelbart, Vancouver (CA)

(73) Assignee: KARDIUM INC. (CA)

( * ) Notice: Subject to any disclaimer, the term of this patent is extended or adjusted under 35 U.S.C. 154(b) by 0 days.

(21) Appl. No.: 14/162,469

(22) Filed: Jan. 23, 2014

(65) Prior Publication Data

US 2014/0135913 A1    May 15, 2014

Related U.S. Application Data

(60) Continuation of application No. 13/872,870, filed on Apr. 29, 2013, now Pat. No. 8,672,998, which is a division of application No. 11/475,978, filed on Jun. 28, 2006, now Pat. No. 8,449,605.

(51) Int. Cl.
*A61F 2/24* (2006.01)

(52) U.S. Cl.
CPC .............. *A61F 2/2418* (2013.01); *A61F 2/2412* (2013.01); *A61F 2/2442* (2013.01); *A61F 2/2451* (2013.01); *A61F 2/2466* (2013.01); *A61F 2/2433* (2013.01); *A61F 2210/009* (2013.01)

(58) Field of Classification Search
CPC ... A61F 2/2451; A61F 2/2448; A61F 2/2418; A61F 2/2412
See application file for complete search history.

(56) References Cited

U.S. PATENT DOCUMENTS

| | | | |
|---|---|---|---|
| 566,521 | A | 8/1896 | Leger |
| 3,132,438 | A | 5/1964 | Ward et al. |
| 4,041,955 | A | 8/1977 | Kelly et al. |
| 4,085,744 | A | 4/1978 | Lewis et al. |
| 4,114,202 | A | 9/1978 | Roy et al. |
| 4,164,046 | A | 8/1979 | Cooley |
| 4,225,148 | A | 9/1980 | Anderson |
| 4,240,441 | A | 12/1980 | Khalil |
| 4,261,342 | A | 4/1981 | Aranguren Duo |
| 4,263,680 | A | 4/1981 | Reul et al. |
| 4,273,128 | A | 6/1981 | Lary |
| 4,411,266 | A | 10/1983 | Cosman |
| 4,490,859 | A | 1/1985 | Black et al. |

(Continued)

FOREIGN PATENT DOCUMENTS

| | | |
|---|---|---|
| EP | 0723467 B1 | 4/2002 |
| EP | 2082690 A1 | 7/2009 |

(Continued)

OTHER PUBLICATIONS

"Constellation Mapping Catheters", Brochure, Boston Scientific Corp., 2 pgs, © 2007 Boston Scientific Corporation.

(Continued)

*Primary Examiner* — Jason-Dennis Stewart
(74) *Attorney, Agent, or Firm* — Rossi, Kimms & McDowell LLP

(57) ABSTRACT

An artificial mitral valve is anchored in the left atrium by placing the valve between the annulus of the natural mitral valve and an artificial annulus. The artificial annulus is formed by inserting a tool into the coronary sinus, and adjusting the tool to force the wall of the left atrium to form an annulus above the artificial valve, this locking it in place and forming a hemostatic seal.

16 Claims, 7 Drawing Sheets

(56) References Cited

U.S. PATENT DOCUMENTS

| | | |
|---|---|---|
| 4,527,554 A | 7/1985 | Klein |
| 4,543,090 A | 9/1985 | McCoy |
| 4,699,147 A | 10/1987 | Chilson et al. |
| 4,770,187 A | 9/1988 | Lash et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,921,499 A | 5/1990 | Hoffman et al. |
| 4,942,788 A | 7/1990 | Farr et al. |
| 4,979,514 A | 12/1990 | Sekii et al. |
| 4,994,698 A | 2/1991 | Kliman et al. |
| 4,998,933 A | 3/1991 | Eggers et al. |
| 5,021,059 A | 6/1991 | Kensey et al. |
| 5,026,384 A | 6/1991 | Farr et al. |
| 5,039,894 A | 8/1991 | Teter et al. |
| 5,047,047 A | 9/1991 | Yoon |
| 5,100,418 A | 3/1992 | Yoon et al. |
| 5,104,399 A | 4/1992 | Lazarus |
| 5,122,137 A | 6/1992 | Lennox |
| 5,127,902 A | 7/1992 | Fischell |
| 5,156,151 A | 10/1992 | Imran |
| 5,156,609 A | 10/1992 | Nakao et al. |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,192,314 A | 3/1993 | Daskalakis |
| 5,201,316 A | 4/1993 | Pomeranz et al. |
| 5,228,442 A | 7/1993 | Imran |
| 5,242,386 A | 9/1993 | Holzer |
| 5,242,456 A | 9/1993 | Nash et al. |
| 5,245,987 A | 9/1993 | Redmond et al. |
| 5,258,000 A | 11/1993 | Glanturco |
| 5,279,299 A | 1/1994 | Imran |
| 5,293,869 A | 3/1994 | Edwards et al. |
| 5,312,435 A | 5/1994 | Nash et al. |
| 5,312,439 A | 5/1994 | Loeb |
| 5,317,952 A | 6/1994 | Immega |
| 5,320,632 A | 6/1994 | Heidmueller |
| 5,341,807 A | 8/1994 | Nardella |
| 5,364,408 A | 11/1994 | Gordon |
| 5,366,443 A | 11/1994 | Eggers et al. |
| 5,366,459 A | 11/1994 | Yoon |
| 5,368,601 A | 11/1994 | Sauer et al. |
| 5,374,275 A | 12/1994 | Bradley et al. |
| 5,379,773 A | 1/1995 | Hornsby |
| RE34,866 E | 2/1995 | Kensey et al. |
| 5,390,664 A | 2/1995 | Redmond et al. |
| 5,417,698 A | 5/1995 | Green et al. |
| 5,419,767 A | 5/1995 | Eggers et al. |
| 5,423,859 A | 6/1995 | Koyfman et al. |
| 5,450,860 A | 9/1995 | O'Connor |
| 5,454,834 A | 10/1995 | Boebel et al. |
| 5,478,353 A | 12/1995 | Yoon |
| 5,496,267 A | 3/1996 | Drasler et al. |
| 5,507,811 A | 4/1996 | Koike et al. |
| 5,531,760 A | 7/1996 | Alwafaie |
| 5,557,967 A | 9/1996 | Renger |
| 5,558,091 A | 9/1996 | Acker et al. |
| 5,575,810 A | 11/1996 | Swanson et al. |
| 5,593,424 A | 1/1997 | Northrup, III |
| 5,598,848 A | 2/1997 | Swanson et al. |
| 5,645,566 A | 7/1997 | Brenneman et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,690,649 A | 11/1997 | Li |
| 5,697,285 A | 12/1997 | Nappi et al. |
| 5,713,896 A | 2/1998 | Nardella |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,752,965 A | 5/1998 | Francis et al. |
| 5,762,066 A | 6/1998 | Law et al. |
| 5,769,846 A | 6/1998 | Edwards et al. |
| 5,782,239 A | 7/1998 | Webster, Jr. |
| 5,782,861 A | 7/1998 | Cragg et al. |
| 5,782,879 A | 7/1998 | Rosborough et al. |
| 5,800,495 A | 9/1998 | Machek et al. |
| 5,824,066 A | 10/1998 | Gross |
| 5,830,222 A | 11/1998 | Makower |
| 5,836,990 A | 11/1998 | Li |
| 5,865,791 A | 2/1999 | Whayne et al. |
| 5,871,505 A | 2/1999 | Adams et al. |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. |
| 5,964,782 A | 10/1999 | Lafontaine et al. |
| 5,971,994 A | 10/1999 | Fritzsch |
| 5,976,174 A | 11/1999 | Ruiz |
| 5,980,473 A | 11/1999 | Korakianitis et al. |
| 5,984,950 A | 11/1999 | Cragg et al. |
| 6,001,069 A | 12/1999 | Tachibana et al. |
| 6,024,096 A | 2/2000 | Buckberg |
| 6,063,082 A | 5/2000 | DeVore et al. |
| 6,074,417 A | 6/2000 | Peredo |
| 6,074,418 A | 6/2000 | Buchanan et al. |
| 6,104,944 A | 8/2000 | Martinelli |
| 6,113,610 A | 9/2000 | Poncet |
| 6,123,702 A | 9/2000 | Swanson et al. |
| 6,132,438 A | 10/2000 | Fleischman et al. |
| 6,138,043 A | 10/2000 | Avitall |
| 6,142,993 A | 11/2000 | Whayne et al. |
| 6,156,046 A | 12/2000 | Passafaro et al. |
| 6,183,496 B1 | 2/2001 | Urbanski |
| 6,203,554 B1 | 3/2001 | Roberts |
| 6,210,432 B1 | 4/2001 | Solem et al. |
| 6,214,032 B1 | 4/2001 | Loeb et al. |
| 6,217,573 B1 | 4/2001 | Webster |
| 6,221,103 B1 | 4/2001 | Melvin |
| 6,221,104 B1 | 4/2001 | Buckberg et al. |
| 6,241,747 B1 | 6/2001 | Ruff |
| 6,248,124 B1 | 6/2001 | Pedros et al. |
| 6,258,258 B1 | 7/2001 | Sartori et al. |
| 6,261,309 B1 | 7/2001 | Urbanski |
| 6,266,550 B1 | 7/2001 | Selmon et al. |
| 6,287,321 B1 | 9/2001 | Jang |
| 6,304,769 B1 | 10/2001 | Arenson et al. |
| 6,306,135 B1 | 10/2001 | Ellman et al. |
| 6,308,091 B1 | 10/2001 | Avitall |
| 6,332,864 B1 | 12/2001 | Schweich, Jr. et al. |
| 6,346,105 B1 | 2/2002 | Tu et al. |
| 6,358,258 B1 | 3/2002 | Arcia et al. |
| 6,358,277 B1 | 3/2002 | Duran |
| 6,360,749 B1 | 3/2002 | Jayaraman |
| 6,379,366 B1 | 4/2002 | Fleischman et al. |
| 6,383,151 B1 | 5/2002 | Diederich et al. |
| 6,389,311 B1 | 5/2002 | Whayne et al. |
| 6,391,048 B1 | 5/2002 | Ginn et al. |
| 6,391,054 B2 | 5/2002 | Carpentier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,409,760 B1 | 6/2002 | Melvin |
| 6,416,459 B1 | 7/2002 | Haindl |
| 6,432,115 B1 | 8/2002 | Mollenauer et al. |
| 6,436,052 B1 | 8/2002 | Nikolic et al. |
| 6,450,171 B1 | 9/2002 | Buckberg et al. |
| 6,475,223 B1 | 11/2002 | Werp et al. |
| 6,485,409 B1 | 11/2002 | Voloshin et al. |
| 6,485,489 B2 | 11/2002 | Teirstein et al. |

(56) References Cited

U.S. PATENT DOCUMENTS

| | | |
|---|---|---|
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,626,930 B1 | 9/2003 | Allen et al. |
| 6,632,238 B2 | 10/2003 | Ginn et al. |
| 6,662,034 B2 | 12/2003 | Segner et al. |
| 6,676,685 B2 | 1/2004 | Pedros et al. |
| 6,681,773 B2 | 1/2004 | Murphy et al. |
| 6,704,590 B2 | 3/2004 | Haldeman |
| 6,723,038 B1 | 4/2004 | Schroeder et al. |
| 6,726,704 B1 | 4/2004 | Loshakove et al. |
| 6,726,716 B2 | 4/2004 | Marquez |
| 6,743,241 B2 | 6/2004 | Kerr |
| 6,749,622 B2 | 6/2004 | McGuckin et al. |
| 6,752,810 B1 | 6/2004 | Gao et al. |
| 6,760,616 B2 | 7/2004 | Hoey et al. |
| 6,780,197 B2 | 8/2004 | Roe et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,840,957 B2 | 1/2005 | DiMatteo et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,941,171 B2 | 9/2005 | Mann et al. |
| 6,942,657 B2 | 9/2005 | Sinofsky et al. |
| 6,949,122 B2 | 9/2005 | Adams et al. |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,991,649 B2 | 1/2006 | Sievers |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,101,395 B2 | 9/2006 | Tremulis et al. |
| 7,141,019 B2 | 11/2006 | Pearlman |
| 7,144,363 B2 | 12/2006 | Pai et al. |
| 7,160,322 B2 | 1/2007 | Gabbay |
| 7,166,127 B2 | 1/2007 | Spence et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,276,044 B2 | 10/2007 | Ferry et al. |
| 7,279,007 B2 | 10/2007 | Nikolic et al. |
| 7,280,863 B2 | 10/2007 | Shachar |
| 7,300,435 B2 | 11/2007 | Wham et al. |
| 7,303,526 B2 | 12/2007 | Sharkey et al. |
| 7,320,665 B2 | 1/2008 | Vijay |
| 7,335,196 B2 | 2/2008 | Swanson et al. |
| 7,374,530 B2 | 5/2008 | Schaller |
| 7,399,271 B2 | 7/2008 | Khairkhahan et al. |
| 7,431,726 B2 | 10/2008 | Spence et al. |
| 7,452,325 B2 | 11/2008 | Schaller |
| 7,452,375 B2 | 11/2008 | Mathis et al. |
| 7,507,252 B2 | 3/2009 | Lashinski et al. |
| 7,513,867 B2 | 4/2009 | Lichtenstein |
| 7,582,051 B2 | 9/2009 | Khairkhahan et al. |
| 7,611,534 B2 | 11/2009 | Kapadia et al. |
| 7,674,276 B2 | 3/2010 | Stone et al. |
| 7,704,277 B2 | 4/2010 | Zakay et al. |
| 7,736,388 B2 | 6/2010 | Goldfarb et al. |
| 7,738,967 B2 | 6/2010 | Salo |
| 7,749,249 B2 | 7/2010 | Gelbart et al. |
| 7,837,610 B2 | 11/2010 | Lichtenstein et al. |
| 7,869,854 B2 | 1/2011 | Shachar et al. |
| 7,873,402 B2 | 1/2011 | Shachar |
| 7,887,482 B2 | 2/2011 | Hamada |
| 8,027,714 B2 | 9/2011 | Shachar |
| 8,128,644 B2 | 3/2012 | Carley et al. |
| 8,150,499 B2 | 4/2012 | Gelbart et al. |
| 8,337,524 B2 | 12/2012 | Gelbart et al. |
| 8,449,605 B2 | 5/2013 | Lichtenstein et al. |
| 8,532,746 B2 | 9/2013 | Gelbart et al. |
| 8,672,998 B2 | 3/2014 | Lichtenstein et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0041915 A1 | 11/2001 | Roue et al. |
| 2001/0044568 A1 | 11/2001 | Langberg et al. |
| 2002/0002329 A1 | 1/2002 | Avitall |
| 2002/0013621 A1 | 1/2002 | Stobie et al. |
| 2002/0016628 A1 | 2/2002 | Langberg |
| 2002/0026092 A1 | 2/2002 | Buckberg et al. |
| 2002/0055775 A1 | 5/2002 | Carpentier et al. |
| 2002/0082621 A1 | 6/2002 | Schurr et al. |
| 2002/0087156 A1 | 7/2002 | Maguire et al. |
| 2002/0087173 A1 | 7/2002 | Alferness et al. |
| 2002/0107478 A1 | 8/2002 | Wendlandt |
| 2002/0107511 A1 | 8/2002 | Collins et al. |
| 2002/0107530 A1 | 8/2002 | Sauer et al. |
| 2002/0111647 A1 | 8/2002 | Khairkhahan et al. |
| 2002/0115944 A1 | 8/2002 | Mendes et al. |
| 2002/0161394 A1 | 10/2002 | Macoviak et al. |
| 2002/0161406 A1 | 10/2002 | Silvian |
| 2002/0169359 A1 | 11/2002 | McCarthy et al. |
| 2002/0169360 A1 | 11/2002 | Taylor et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2002/0198603 A1 | 12/2002 | Buckberg et al. |
| 2003/0018358 A1 | 1/2003 | Saadat |
| 2003/0023241 A1 | 1/2003 | Drewry et al. |
| 2003/0028202 A1 | 2/2003 | Sancoff et al. |
| 2003/0036755 A1 | 2/2003 | Ginn |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078652 A1 | 4/2003 | Sutherland |
| 2003/0078671 A1 | 4/2003 | Lesniak et al. |
| 2003/0083742 A1 | 5/2003 | Spence et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0124480 A1 | 7/2003 | Peacock |
| 2003/0149333 A1 | 8/2003 | Alferness |
| 2003/0158570 A1 | 8/2003 | Ferrazzi |
| 2003/0163191 A1 | 8/2003 | Nikolic et al. |
| 2003/0167055 A1 | 9/2003 | Kolata et al. |
| 2003/0181819 A1 | 9/2003 | Desai |
| 2003/0208210 A1 | 11/2003 | Dreyfuss et al. |
| 2003/0212453 A1 | 11/2003 | Mathis et al. |
| 2003/0220667 A1 | 11/2003 | Van der Burg et al. |
| 2003/0229395 A1 | 12/2003 | Cox |
| 2004/0002626 A1 | 1/2004 | Feld et al. |

(56) References Cited

U.S. PATENT DOCUMENTS

| | | |
|---|---|---|
| 2004/0054279 A1 | 3/2004 | Hanley |
| 2004/0122516 A1 | 6/2004 | Fogarty et al. |
| 2004/0127916 A1 | 7/2004 | Bolduc et al. |
| 2004/0133220 A1 | 7/2004 | Lashinski et al. |
| 2004/0133273 A1 | 7/2004 | Cox |
| 2004/0138529 A1 | 7/2004 | Wiltshire et al. |
| 2004/0138744 A1 | 7/2004 | Lashinski et al. |
| 2004/0138745 A1 | 7/2004 | Macoviak et al. |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0176797 A1 | 9/2004 | Opolski |
| 2004/0176800 A1 | 9/2004 | Paraschac et al. |
| 2004/0186566 A1 | 9/2004 | Hindrichs et al. |
| 2004/0193187 A1 | 9/2004 | Boehringer et al. |
| 2004/0215232 A1 | 10/2004 | Belhe et al. |
| 2004/0220593 A1 | 11/2004 | Greenhalgh |
| 2004/0236419 A1 | 11/2004 | Milo |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0260390 A1 | 12/2004 | Sarac et al. |
| 2004/0260393 A1 | 12/2004 | Rahdert et al. |
| 2004/0267191 A1 | 12/2004 | Gifford, III et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0038509 A1 | 2/2005 | Ashe |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0075727 A1 | 4/2005 | Wheatley |
| 2005/0080402 A1 | 4/2005 | Santamore et al. |
| 2005/0090840 A1 | 4/2005 | Gerbino et al. |
| 2005/0096047 A1 | 5/2005 | Haberman et al. |
| 2005/0096498 A1 | 5/2005 | Houser et al. |
| 2005/0096589 A1 | 5/2005 | Shachar |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0131441 A1 | 6/2005 | Iio et al. |
| 2005/0137659 A1 | 6/2005 | Garabedian et al. |
| 2005/0137689 A1 | 6/2005 | Salahieh et al. |
| 2005/0137700 A1 | 6/2005 | Spence et al. |
| 2005/0143809 A1 | 6/2005 | Salahieh et al. |
| 2005/0148892 A1 | 7/2005 | Desai |
| 2005/0149014 A1 | 7/2005 | Hauck et al. |
| 2005/0149114 A1 | 7/2005 | Cartledge et al. |
| 2005/0154252 A1 | 7/2005 | Sharkey et al. |
| 2005/0177180 A1 | 8/2005 | Kaganov et al. |
| 2005/0177227 A1 | 8/2005 | Heim et al. |
| 2005/0182365 A1 | 8/2005 | Hennemann et al. |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0197716 A1 | 9/2005 | Sharkey et al. |
| 2005/0203558 A1 | 9/2005 | Maschke |
| 2005/0209636 A1 | 9/2005 | Widomski et al. |
| 2005/0216052 A1 | 9/2005 | Mazzocchi et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0267573 A9 | 12/2005 | Macoviak et al. |
| 2005/0267574 A1 | 12/2005 | Cohn et al. |
| 2005/0273138 A1 | 12/2005 | To et al. |
| 2006/0004424 A1 | 1/2006 | Loeb et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025784 A1 | 2/2006 | Starksen et al. |
| 2006/0025800 A1 | 2/2006 | Suresh |
| 2006/0030881 A1 | 2/2006 | Sharkey et al. |
| 2006/0052867 A1 | 3/2006 | Revuelta et al. |
| 2006/0058871 A1 | 3/2006 | Zakay et al. |
| 2006/0085049 A1 | 4/2006 | Cory et al. |
| 2006/0135968 A1 | 6/2006 | Schaller |
| 2006/0135970 A1 | 6/2006 | Schaller |
| 2006/0173536 A1 | 8/2006 | Mathis et al. |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0241334 A1 | 10/2006 | Dubi et al. |
| 2006/0241745 A1 | 10/2006 | Solem |
| 2006/0264980 A1 | 11/2006 | Khairkhahan et al. |
| 2006/0276683 A1 | 12/2006 | Feld et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0010817 A1 | 1/2007 | de Coninck |
| 2007/0016006 A1 | 1/2007 | Shachar |
| 2007/0016068 A1 | 1/2007 | Grunwald et al. |
| 2007/0016288 A1 | 1/2007 | Gurskis et al. |
| 2007/0027533 A1 | 2/2007 | Douk |
| 2007/0038208 A1 | 2/2007 | Kefer |
| 2007/0050019 A1 | 3/2007 | Hyde |
| 2007/0060895 A1 | 3/2007 | Sibbitt et al. |
| 2007/0083076 A1 | 4/2007 | Lichtenstein |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0135826 A1 | 6/2007 | Zaver et al. |
| 2007/0135913 A1 | 6/2007 | Moaddeb et al. |
| 2007/0156233 A1 | 7/2007 | Kapadia et al. |
| 2007/0161846 A1 | 7/2007 | Nikolic et al. |
| 2007/0185571 A1 | 8/2007 | Kapadia et al. |
| 2007/0198057 A1 | 8/2007 | Gelbart et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0219460 A1 | 9/2007 | Goldenberg |
| 2007/0225736 A1 | 9/2007 | Zeiner et al. |
| 2007/0249999 A1 | 10/2007 | Sklar et al. |
| 2007/0250160 A1 | 10/2007 | Rafiee |
| 2007/0270681 A1 | 11/2007 | Phillips et al. |
| 2007/0270688 A1 | 11/2007 | Gelbart et al. |
| 2007/0270943 A1 | 11/2007 | Solem et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0033541 A1 | 2/2008 | Gelbart et al. |
| 2008/0045778 A1 | 2/2008 | Lichtenstein et al. |
| 2008/0051802 A1 | 2/2008 | Schostek et al. |
| 2008/0071298 A1 | 3/2008 | Khairkhahan et al. |
| 2008/0086164 A1 | 4/2008 | Rowe |
| 2008/0132915 A1 | 6/2008 | Buckman et al. |
| 2008/0133002 A1 | 6/2008 | Gelbart et al. |
| 2008/0140188 A1 | 6/2008 | Rahdert et al. |
| 2008/0177300 A1 | 7/2008 | Mas et al. |
| 2008/0228266 A1 | 9/2008 | McNamara et al. |
| 2008/0262609 A1 | 10/2008 | Gross et al. |
| 2008/0269785 A1 | 10/2008 | Lampropoulos et al. |
| 2008/0275477 A1 | 11/2008 | Sterrett et al. |
| 2008/0288060 A1 | 11/2008 | Kaye et al. |
| 2008/0312713 A1 | 12/2008 | Wilfley et al. |
| 2009/0076597 A1 | 3/2009 | Dahlgren et al. |
| 2009/0131930 A1 | 5/2009 | Gelbart et al. |
| 2009/0157058 A1 | 6/2009 | Ferren et al. |
| 2009/0192441 A1 | 7/2009 | Gelbart et al. |
| 2009/0192527 A1 | 7/2009 | Messas |

(56) References Cited

U.S. PATENT DOCUMENTS

| | | |
|---|---|---|
| 2009/0192539 A1 | 7/2009 | Lichtenstein |
| 2009/0204180 A1 | 8/2009 | Gelbart |
| 2009/0287304 A1 | 11/2009 | Dahlgren et al. |
| 2010/0087836 A1 | 4/2010 | Jaramillo et al. |
| 2010/0087837 A1 | 4/2010 | Jaramillo et al. |
| 2010/0161047 A1 | 6/2010 | Cabiri |
| 2010/0222789 A1 | 9/2010 | Gelbart et al. |
| 2011/0022166 A1 | 1/2011 | Dahlgren et al. |
| 2011/0082538 A1 | 4/2011 | Dahlgren et al. |
| 2011/0087203 A1 | 4/2011 | Lichtenstein et al. |
| 2011/0087227 A1 | 4/2011 | Mazur et al. |
| 2011/0125172 A1 | 5/2011 | Gelbart et al. |
| 2011/0172658 A1 | 7/2011 | Gelbart et al. |
| 2011/0301618 A1 | 12/2011 | Lichtenstein |
| 2012/0083806 A1 | 4/2012 | Goertzen |
| 2012/0158016 A1 | 6/2012 | Gelbart et al. |
| 2012/0245604 A1 | 9/2012 | Tegzes |
| 2013/0041405 A1 | 2/2013 | Gelbart et al. |
| 2013/0238089 A1 | 9/2013 | Lichtenstein et al. |
| 2013/0345797 A1 | 12/2013 | Dahlgren et al. |
| 2014/0135913 A1 | 5/2014 | Lichtenstein et al. |

FOREIGN PATENT DOCUMENTS

| | | | |
|---|---|---|---|
| WO | 90/15582 A1 | 12/1990 | |
| WO | 95/10320 A1 | 4/1995 | |
| WO | 01/78625 A1 | 10/2001 | |
| WO | 03/015611 A2 | 2/2003 | |
| WO | 03/077800 A1 | 9/2003 | |
| WO | 2004/012629 A1 | 2/2004 | |
| WO | 2004/047679 A1 | 6/2004 | |
| WO | 2004/084746 A2 | 10/2004 | |
| WO | WO 2004084746 A2 * | 10/2004 | ............ A61B 18/00 |
| WO | 2004/100803 A1 | 11/2004 | |
| WO | 2005/007031 A2 | 1/2005 | |
| WO | 2005/046520 A2 | 5/2005 | |
| WO | 2005/070330 A1 | 8/2005 | |
| WO | 2005/102181 A1 | 11/2005 | |
| WO | 2006/017809 A2 | 2/2006 | |
| WO | 2006/105121 A2 | 10/2006 | |
| WO | 2006/135747 A2 | 12/2006 | |
| WO | 2006/135749 A2 | 12/2006 | |
| WO | 2007/021647 A2 | 2/2007 | |
| WO | 2007/115390 A1 | 10/2007 | |
| WO | 2008/002606 A2 | 1/2008 | |
| WO | 2009/065042 A2 | 5/2009 | |

OTHER PUBLICATIONS

"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].

"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.

Becker, et al., "Ablation of Atrial Fibrillation: Energy Sources and Navigation Tools: A Review", Journal of Electrocardiology, vol. 37, Supplement 2004, pp. 55-62, 2004.

Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].

Calkins, Hugh, "Electrophysiology: Radiofrequency Catheter Ablation of Supraventricular Arrhythmias", Heart, 2001; 85; pp. 594-600.

Dahlgren et al., "Medical Device for Constricting Tissue or a Bodily Orifice, for Example a Mitral Valve", Amendment filed Jul. 23, 2013 for U.S. Appl. No. 12/899,407, 60 pages.

Dahlgren et al., "System for Mechanical Adjustment of Medical Implants", Amendment filed Apr. 2, 2010 for U.S. Appl. No. 11/902,099, 19 pgs.

Dahlgren et al., "System for Mechanical Adjustment of Medical Implants", Amendment filed Nov. 1, 2010 for U.S. Appl. No. 11/902,099, 12 pgs.

Dahlgren et al., "System for Mechanical Adjustment of Medical Implants", Office Action mailed Jul. 8, 2010 for U.S. Appl. No. 11/902,099, 37 pgs.

Dahlgren et al., "System for Mechanical Adjustment of Medical Implants", Office Action mailed Oct. 5, 2009 for U.S. Appl. No. 11/902,099, 13 pgs.

De Ponti, et al., "Non-Fluoroscopic Mapping Systems for Electrophysiology: the Tool or Toy Dilemma After 10 Years", European Heart Journal, 2006; 27, pp. 1134-1136.

European Search Report, mailed Jun. 26, 2008 for EP 08100878.1, 11 pgs.

Gabriel, et al., "The Dielectric Properties of Biological Tissues: I. Literature Survey", Phys. Med. Biol.; 41, 1996, pp. 2231-2249.

Gelbart et al., "Automatic Atherectomy System", Amendment filed Sep. 15, 2011 for U.S. Appl. No. 12/950,871, 21 pgs.

Gelbart et al., "Automatic Atherectomy System", Office Action mailed Jun. 15, 2011 for U.S. Appl. No. 12/950,871, 16 pgs.

Gelbart et al., "Automatic Atherectomy System", Office Action mailed Sep. 25, 2012 for U.S. Appl. No. 13/404,834, 24 pgs.

Gelbart et al., "Intra-Cardiac Mapping and Ablation Method", Amendment filed Feb. 23, 2011 for U.S. Appl. No. 11/475,950, 28 pgs.

Gelbart et al., "Intra-Cardiac Mapping and Ablation Method", Amendment filed Mar. 5, 2008 for U.S. Appl. No. 11/475,950, 11 pgs.

Gelbart et al., "Intra-Cardiac Mapping and Ablation Method", Amendment filed Aug. 16, 2010 for U.S. Appl. No. 11/475,950, 22 pgs.

Gelbart et al., "Intra-Cardiac Mapping and Ablation Method", Office Action mailed Nov. 23, 2010 for U.S. Appl. No. 11/475,950, 25 pgs.

Gelbart et al., "Intra-Cardiac Mapping and Ablation Method", Office Action mailed Jun. 23, 2010 for U.S. Appl. No. 11/475,950, 18 pgs.

Gelbart et al., "Intra-Cardiac Mapping and Ablation Method", Pre Amend filed Aug. 29, 2007 for U.S. Appl. No. 11/475,950, 42 pgs.

Gelbart et al., "Liposuction System", Amendment filed Dec. 7, 2011 for U.S. Appl. No. 12/010,458, 15 pgs.

Gelbart et al., "Liposuction System", Amendment filed Jun. 10, 2011 for U.S. Appl. No. 12/010,458, 10 pgs.

Gelbart et al., "Liposuction System", Office Action mailed Mar. 16, 2011 for U.S. Appl. No. 12/010,458, 12 pgs.

Gelbart et al., "Liposuction System", Office Action mailed Sep. 14, 2011 for U.S. Appl. No. 12/010,458, 9 pgs.

Gelbart et al., "Medical Device for Use in Bodily Lumens, for Example an Atrium", Office Action mailed Jul. 25, 2011 for U.S. Appl. No. 11/941,819, 9 pgs.

Gelbart, "System for Implanting a Microstimulator", Amendment filed Jan. 20, 2010 for U.S. Appl. No. 12/068,878, 26 pgs.

Gelbart, "System for Implanting a Microstimulator", Office Action mailed Aug. 18, 2010 for U.S. Appl. No. 12/068,878, 11 pgs.

Gelbart, "System for Implanting a Microstimulator", Office Action mailed Aug. 20, 2009 for U.S. Appl. No. 12/068,878, 12 pgs.

International Preliminary Report on Patentability, issued Jan. 6, 2009 for PCT/US2007/014902, 8 pages.

International Search Report mailed Dec. 6, 2004 for PCT/IB2004/002581, 3 pgs.

International Search Report mailed Sep. 10, 2010 for PCT/US2010/021835, 4 pgs.

International Search Report, mailed Dec. 2, 2009 for PCT/US2008/083644, 4 pages.

International Search Report, mailed Dec. 5, 2007 for PCT/US2007/014902, 4 pages.

Jaramillo et al, "Surgical Instrument and Method for Tensioning and Securing a Flexible Suture", Amendment filed Dec. 4, 2012 for U.S. Appl. No. 12/436,926, 19 pgs.

Jaramillo et al, "Surgical Instrument and Method for Tensioning and Securing a Flexible Suture", Amendment filed Feb. 27, 2012 for U.S. Appl. No. 12/436,926, 25 pgs.

Jaramillo et al, "Surgical Instrument and Method for Tensioning and Securing a Flexible Suture", Amendment filed Jul. 26, 2011 for U.S. Appl. No. 12/246,614, 41 pgs.

Jaramillo et al, "Surgical Instrument and Method for Tensioning and Securing a Flexible Suture", Amendment filed Mar. 14, 2011 for U.S. Appl. No. 12/246,614, 22 pgs.

(56) References Cited

OTHER PUBLICATIONS

Jaramillo et al, "Surgical Instrument and Method for Tensioning and Securing a Flexible Suture", Amendment filed Oct. 5, 2011 for U.S. Appl. No. 12/436,926, 77 pgs.
Jaramillo et al, "Surgical Instrument and Method for Tensioning and Securing a Flexible Suture", Office Action mailed Dec. 13, 2010 for U.S. Appl. No. 12/246,614, 15 pgs.
Jaramillo et al, "Surgical Instrument and Method for Tensioning and Securing a Flexible Suture", Office Action mailed Jan. 11, 2012 for U.S. Appl. No. 12/436,926, 26 pgs.
Jaramillo et al, "Surgical Instrument and Method for Tensioning and Securing a Flexible Suture", Office Action mailed Jul. 8, 2011 for U.S. Appl. No. 12/436,926, 17 pgs.
Jaramillo et al, "Surgical Instrument and Method for Tensioning and Securing a Flexible Suture", Office Action mailed May 27, 2011 for U.S. Appl. No. 12/246,614, 24 pgs.
Jaramillo et al, "Surgical Instrument and Method for Tensioning and Securing a Flexible Suture", Office Action mailed Sep. 21, 2012 for U.S. Appl. No. 12/436,926, 14 pgs.
Lichtenstein et al., "System for Improving Diastolic Dysfunction", Office Action mailed Sep. 18, 2012 for U.S. Appl. No. 12/904,885, 15 pgs.
Lichtenstein et al., "System for Improving Diastolic Dysfunction", Preliminary Amendment filed Oct. 14, 2010 for U.S. Appl. No. 12/904,885, 23 pgs.
Lichtenstein, "Methods and Devices for Altering Blood Flow Through the Left Ventricle", Amendment filed Jul. 26, 2007 for U.S. Appl. No. 10/622,129, 17 pages.
Lichtenstein, "Methods and Devices for Altering Blood Flow Through the Left Ventricle", Examiner's Amendment mailed Mar. 2, 2009 for U.S. Appl. No. 10/622,129, 5 pages.
Extended European Search Report mailed Sep. 18, 2014 for EP 10821276.2, 10 pages.
Gelbart et al., "Automatic Atherectomy System", Notice of Allowance mailed May 10, 2013 and Certificate of Correction mailed May 6, 2014 for U.S. Appl. No. 13/404,834, 11 pgs.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance mailed Aug. 20, 2010 for U.S. Appl. No. 11/436,584, 12 pgs.
Gelbart et al., "Automatic Atherectomy System", Notice of Allowance mailed Nov. 25, 2011 and Certificate of Correction mailed Jul. 17, 2012 for U.S. Appl. No. 12/950,871, 24 pgs.
Gelbart et al., "Method and Device for Closing Holes in Tissue", Response to Quayle Action filed Jul. 14, 2014 for U.S. Appl. No. 13/652,299, 29 pages.
Gelbart et al., "Method and Device for Closing Holes in Tissue", Quayle Action mailed May 20, 2014 for U.S. Appl. No. 13/652,299, 25 pages.
Gelbart et al., "Method and Device for Closing Holes in Tissue", Preliminary Amendment fiiled Feb. 21, 2013 for U.S. Appl. No. 13/652,299, 9 pages.
Gelbart et al., "Method and Device for Closing Holes in Tissue", Notice of Allowance mailed Feb. 24, 2010, Supplemental Notice of Allowance mailed Mar. 24, 2010 and Remarks filed after allowance on Apr. 9, 2010 for U.S. Appl. No. 11/436,585, 20 pgs.
Gelbart et al., "Method and Device for Closing Holes in Tissue", Notice of Allowance mailed Aug. 22, 2012 for U.S. Appl. No. 12/777,883, 12 pgs.
Goertzen et al., "Tissue Anchor System", Notice of Allowance mailed Jul. 7, 2014 for U.S. Appl. No. 13/247,380, 8 pgs.
Goertzen et al., "Tissue Anchor System", Notice of Allowance mailed Oct. 16, 2014 for U.S. Appl. No. 13/247,380, 41 pgs.
Lichtenstein et al., "Method for Anchoring a Mitral Valve", Notices of Allowance mailed Oct. 2, 2013 and Nov. 13, 2013 for U.S. Appl. No. 13/872,870, 35 pgs.
Lichtenstein et al., "Method for Anchoring a Mitral Valve", Notice of Allowance mailed Jan. 28, 2013 for U.S. Appl. No. 11/475,978, 24 pgs.
Lichtenstein et al., "System for Improving Diastolic Dysfunction", Notice of Allowance mailed Jul. 12, 2010 for U.S. Appl. No. 11/497,309, 8 pgs.
Lichtenstein et al., "System for Improving Diastolic Dysfunction", Office Action mailed Jan. 29, 2014 for U.S. Appl. No. 12/904,885, 38 pgs.
Lichtenstein et al., "System for Improving Diastolic Dysfunction", Amendment filed Apr. 9, 2014 for U.S. Appl. No. 12/904,885, 24 pgs.
Lichtenstein et al., "System for Improving Diastolic Dysfunction", Amendment filed Dec. 18, 2012 for U.S. Appl. No. 12/904,885, 23 pgs.
Lichtenstein, "Closing Openings in Anatomical Tissue", Final Office Action mailed Dec. 4, 2013 for U.S. Appl. No. 13/112,695, 31 pages.
Lichtenstein, "Methods and Devices for Altering Blood Flow Through the Left Ventricle", Office Action mailed Jul. 9, 2010 for U.S. Appl. No. 10/571,165, 11 pages.
Lichtenstein, "Methods and Devices for Altering Blood Flow Through the Left Ventricle", Office Action mailed Mar. 26, 2007 for U.S. Appl. No. 10/622,129, 17 pages.
Lichtenstein, "Methods and Devices for Altering Blood Flow Through the Left Ventricle", Office Action mailed Nov. 14, 2007 for U.S. Appl. No. 10/622,129, 6 pages.
Lichtenstein, "Methods and Devices for Altering Blood Flow Through the Left Ventricle", Preliminary Amendment filed Feb. 14, 2008 for U.S. Appl. No. 10/622,129, 15 pages.
Lichtenstein, "Methods and Devices for Altering Blood Flow Through the Left Ventricle", Preliminary Amendment filed Mar. 6, 2006 for U.S. Appl. No. 10/571,165, 7 pages.
Lopes et al., "Enhanced Medical Device for Use in Bodily Cavities, for Example an Atrium", U.S. Appl. No. 61/435,213, filed Jan. 21, 2011, 320 pgs.
Lopes et al., "Enhanced Medical Device for Use in Bodily Cavities, for Example an Atrium", U.S. Appl. No. 61/485,987, filed May 13, 2011, 401 pgs.
Lopes et al., "Enhanced Medical Device for Use in Bodily Cavities, for Example an Atrium", U.S. Appl. No. 61/488,639, filed May 20, 2011, 434 pgs.
Lopes et al., "Enhanced Medical Device for Use in Bodily Cavities, for Example an Atrium", U.S. Appl. No. 61/515,141, filed Aug. 4, 2011, 508 pgs.
STAR Closure System Brochure, 2005, Abbott Vascular, pp. 1-4.
Tegzes, "Medical Kit for Constricting Tissue or a Bodily Orifice, for Example, a Mitral Valve", Office Action mailed Jul. 11, 2014 for U.S. Appl. No. 13/421,677, 9 pgs.
Written Opinion, mailed Dec. 5, 2007, for PCT/US2007/014902, 7 pages.
Written Opinion mailed Dec. 6, 2004 for PCT/IB2004/002581, 8 pgs.
Written Opinion mailed Sep. 10, 2010 for PCT/US2010/021835, 6 pgs.
Written Opinion mailed Dec. 2, 2009, for PCT/US2008/083644, 9 pages.
Dahlgren et al., "Medical Device, Kit and Method for Constricting Tissue or a Bodily Orifice, for Example, a Mitral Valve", Office Action mailed Jul. 9, 2014 for U.S. Appl. No. 13/917,469, 37 pgs.
Dahlgren et al., "Medical Device for Constricting Tissue or a Bodily Orifice, for Example a Mitral Valve", Amendment filed Aug. 8, 2013 for U.S. Appl. No. 12/899,407, 65 pages.
Dahlgren et al., "Medical Device for Constricting Tissue or a Bodily Orifice, for Example a Mitral Valve", Amendment filed Dec. 13, 2012 for U.S. Appl. No. 12/899,407, 22 pages.
Dahlgren et al., "Medical Device for Constricting Tissue or a Bodily Orifice, for Example a Mitral Valve", Office Action mailed Mar. 8, 2013 for U.S. Appl. No. 12/899,407, 23 pages.
Dahlgren et al., "Medical Device, Kit and Method for Constricting Tissue or a Bodily Orifice, for Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, for Example a Mitral Valve", Final Office Action mailed Feb. 13, 2013 for U.S. Appl. No. 12/894,912, 35 pgs.
Dahlgren et al., "Medical Device, Kit and Method for Constricting Tissue or a Bodily Orifice, for Example a Mitral Valve", Office Action mailed Aug. 30, 2012 for U.S. Appl. No. 12/894,912, 16 pgs.

(56) References Cited

OTHER PUBLICATIONS

Dahlgren et al., "Medical Device, Kit and Method for Constricting Tissue or a Bodily Orifice, for Example a Mitral Valve", Response filed Jun. 13, 2013 for U.S. Appl. No. 12/894,912, 3 pgs.
Gelbart et al., "Automatic Atherectomy System", Amendment filed Oct. 25, 2010 for U.S. Appl. No. 11/436,584, 9 pgs.
Gelbart et al., "Automatic Atherectomy System", Amendment filed Mar. 30, 2010 for U.S. Appl. No. 11/436,584, 20 pgs.
Gelbart et al., "Automatic Atherectomy System", Amendment filed Aug. 4, 2009 for U.S. Appl. No. 11/436,584, 35 pgs.
Gelbart et al., "Automatic Atherectomy System", Office Action mailed Dec. 14, 2010 for U.S. Appl. No. 11/436,584, 12 pgs.
Goertzen et al., "Tissue Anchor System", Amendment filed Dec. 10, 2013 for U.S. Appl. No. 13/247,380, 11 pgs.
Goertzen et al., "Tissue Anchor System", Amendment filed Oct. 11, 2013 for U.S. Appl. No. 13/247,380, 10 pgs.
Dahlgren et al., "Medical Device, Kit and Method for Constricting Tissue or a Bodily Orifice, for Example, a Mitral Valve", Office Action mailed Mar. 5, 2015 for U.S. Appl. No. 13/917,469, 52 pgs.
Gelbart et al., "Method and Device for Closing Holes in Tissue", Amendment filed Feb. 5, 2015 for U.S. Appl. No. 13/652,299, 11 pages.
Athanasuleas et al., "Surgical Anterior Ventricular Restoration for Ischemic Cardiomyopathy," *Operative Techniques in Thoracic and Cardiovascular Surgery* 7(2):66-75, May 2002.
Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007, 23 pages.
Cardiac Implants, URL=http://nmtmedical.com/products/ci/index.htm, download date May 13, 2006, 1 page.
Cooley, "Ventricular Aneurysms and Akinesis," *Cleveland Clinic Quarterly* 45(1):130-132, 1978.
Dahlgren et al., "Medical Device for Constricting Tissue or a Bodily Orifice, for Example a Mitral Valve," Office Action mailed Dec. 18, 2009, for U.S. Appl. No. 12/120,195, 9 pages.
Dahlgren et al., "Medical Device for Constricting Tissue or a Bodily Orifice, for Example a Mitral Valve," Amendment filed Apr. 13, 2010, for U.S. Appl. No. 12/120,195, 22 pages.
Dahlgren et al., "Medical Device for Constricting Tissue or a Bodily Orifice, for Example a Mitral Valve," Office Action mailed Jul. 7, 2010, for U.S. Appl. No. 12/120,195, 14 pages.
Dahlgren et al., "Medical Device for Constricting Tissue or a Bodily Orifice, for Example a Mitral Valve," Preliminary Amendment filed Oct. 6, 2010 for U.S. Appl. No. 12/899,407, 8 pages.
Dahlgren et al., "Medical Device for Constricting Tissue or a Bodily Orifice, for Example a Mitral Valve," Office Action mailed Sep. 13, 2012 for U.S. Appl. No. 12/899,407, 10 pages.
Dahlgren et al., "Medical Device, Kit and Method for Constricting Tissue or a Bodily Orifice, for Example a Mitral Valve," U.S. Appl. No. 61/278,232, filed Oct. 1, 2009, 214 pages.
David et al., "Postinfarction Ventricular Septal Rupture: Repair by Endocardial Patch with Infarct Exclusion," *Journal of Thoracic and Card Surgery* 110(5):1315-1322, 1995.
Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.
Dor et al., "Left Ventricular Aneurysm: A New Surgical Approach," *Thoracic Cardiovascular Surgery* 37:11-19, 1989.
Dor, "Left Ventricular Aneurysms: The Endoventricular Circular Patch Plasty," *Seminars in Thoracic and Cardiovascular Surgery* 9(2):123-130, Apr. 1997.
Gelbart et al., "Artificial Valve," Office Action mailed May 7, 2010 for U.S. Appl. No. 11/497,306, 12 pages.
Gelbart et al., "Artificial Valve," Preliminary Amendment filed Jan. 29, 2010 for U.S. Appl. No. 11/497,306, 22 pages.
Gelbart et al., "Automatic Atherectomy System," Office Action mailed Mar. 4, 2009 for U.S. Appl. No. 11/436,584, 7 pages.
Gelbart et al., "Method and Device for Closing Holes in Tissue," Office Action mailed Sep. 4, 2008, for U.S. Appl. No. 11/436,585, 8 pages.
Gelbart et al., "Method and Device for Closing Holes in Tissue," Amendment filed Sep. 22, 2008, for U.S. Appl. No. 11/436,585, 3 pages.
Gelbart et al., "Method and Device for Closing Holes in Tissue," Office Action mailed Jan. 2, 2009, for U.S. Appl. No. 11/436,585, 11 pages.
Gelbart et al., "Method and Device for Closing Holes in Tissue," Amendment filed Jan. 30, 2009, for U.S. Appl. No. 11/436,585, 5 pages.
Gelbart et al., "Method and Device for Closing Holes in Tissue," Amendment filed Jun. 2, 2009, for U.S. Appl. No. 11/436,585, 7 pages.
Gelbart et al., "Method and Device for Closing Holes in Tissue," Office Action mailed Jul. 7, 2009, for U.S. Appl. No. 11/436,585, 9 pages.
Gelbart et al., "Method and Device for Closing Holes in Tissue," Amendment filed Oct. 26, 2009, for U.S. Appl. No. 11/436,585, 13 pages.
Gelbart et al., "Method and Device for Closing Holes in Tissue," Office Action mailed Feb. 23, 2012 for U.S. Appl. No. 12/777,883, 8 pages.
Gelbart et al., "Method and Device for Closing Holes in Tissue," Amendment filed May 4, 2012 for U.S. Appl. No. 12/777,883, 12 pages.
Goertzen et al., "Tissue Anchor System," Amendment filed Apr. 29, 2013, for U.S. Appl. No. 13/247,380, 22 pages.
Goertzen et al., "Tissue Anchor System," Office Action mailed Jan. 29, 2013, for U.S. Appl. No. 13/247,380, 10 pages.
Goertzen et al., "Tissue Anchor System," Office Action mailed Aug. 13, 2013, for U.S. Appl. No. 13/247,380, 15 pages.
International Search Report, mailed Jan. 8, 2007, for PCT/CA2006/001123, 5 pages.
International Search Report, mailed Jun. 16, 2011, for PCT/US2010/050945, 5 pages.
International Search Report, mailed Sep. 4, 2009, for PCT/US2009/043612, 7 pages.
Jatene, "Left Ventricular Aneurysmectomy," *Journal of Thoracic and Cardiovascular Surgery* 89(3):321-331, 1985.
Konings et al., "Development of an Intravascular Impedance Catheter for Detection of Fatty Lesions in Arteries," *IEEE Transactions on Medical Imaging*, 16(4):439-446, 1997.
Lichtenstein, "Closing Openings in Anatomical Tissue," Office Action mailed May 8, 2013, for U.S. Appl. No. 13/112,695, 12 pages.
Lichtenstein, "Closing Openings in Anatomical Tissue," Amendment filed Aug. 8, 2013, for U.S. Appl. No. 13/112,695, 23 pages.
Lichtenstein, "Method and Apparatus for Percutaneous Reduction of Anterior-Posterior Diameter of Mitral Valve," U.S. Appl. No. 10/690,131, filed Oct. 20, 2003, 31 pages.
Lichtenstein, "Method and Apparatus for Percutaneous Reduction of Anterior-Posterior Diameter of Mitral Valve," Office Action mailed May 15, 2006, for U.S. Appl. No. 10/690,131, 9 pages.
Lichtenstein, "Method and Apparatus for Percutaneous Reduction of Anterior-Posterior Diameter of Mitral Valve," Office Action mailed Dec. 1, 2008, for U.S. Appl. No. 11/400,260, 10 pages.
Lichtenstein et al, "Method for Anchoring a Mitral Valve," Amendment filed Aug. 31, 2009, for U.S. Appl. No. 11/475,978, 24 pages.
Lichtenstein et al, "Method for Anchoring a Mitral Valve," Amendment filed Mar. 26, 2010, for U.S. Appl. No. 11/475,978, 26 pages.
Lichtenstein et al, "Method for Anchoring a Mitral Valve," Office Action mailed Dec. 29, 2009, for U.S. Appl. No. 11/475,978, 7 pages.
Lichtenstein et al., "Method for Anchoring a Mitral Valve," Office Action mailed May 1, 2009, for U.S. Appl. No. 11/475,978, 6 pages.
Lichtenstein et al., "System for Improving Diastolic Dysfunction," Office Action mailed Dec. 24, 2008 for U.S. Appl. No. 11/497,309, 8 pages.
Lichtenstein et al., "System for Improving Diastolic Dysfunction," Amendment filed Apr. 22, 2009 for U.S. Appl. No. 11/497,309, 23 pages.

(56) References Cited

OTHER PUBLICATIONS

Lichtenstein et al., "System for Improving Diastolic Dysfunction," Office Action mailed Aug. 5, 2009 for U.S. Appl. No. 11/497,309, 10 pages.
Lichtenstein et al., "System for Improving Diastolic Dysfunction," Amendment filed Oct. 23, 2009 for U.S. Appl. No. 11/497,309, 9 pages.
Lichtenstein et al., "System for Improving Diastolic Dysfunction," Office Action mailed Jan. 20, 2010 for U.S. Appl. No. 11/497,309, 10 pages.
Lichtenstein et al., "System for Improving Diastolic Dysfunction," Amendment filed Apr. 7, 2010 for U.S. Appl. No. 11/497,309, 8 pages.
Mack, "New Techniques for Percutaneous Repair of the Mitral Valve," *Heart Failure Review*, 11:259-268, 2006.
Mazur et al., "Bone Fixation Device, Tools and Methods," U.S. Appl. No. 61/138,920, filed Dec. 18, 2008, 88 pages.
Menicanti et al., "The Dor Procedure: What has Changed After Fifteen Years of Clinical Practice?" *Journal of Thoracic and Cardiovascular Surgery* 124(5):886-890, Nov. 2002.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Rivera et al., "Ventricular Aneurysms and Akinesis," *Cleveland Clinic Quarterly* 45(1):133-135, 1978.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Tegzes, "Medical Kit for Constricting Tissue or a Bodily Orifice, for Example, a Mitral Valve," U.S. Appl. No. 61/467,883, filed Mar. 25, 2011, 167 pages.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.
Timek et al., "Septal-Lateral Annular Cinching Abolishes Acute Ischemic Mitral Regurgitation," *Journal of Thoracic and Cardiovascular Surgery*, 123(5):881-888, 2002.
Torrent-Guasp et al., "Spatial Orientation of the Ventricular Muscle Band and Approach to Partial Ventriculotomy in Heart Failure," Pathogenesis and Treatment, Ch. 36, pp. 685-693, 2002.
Valvano et al., "Thermal Conductivity and Diffusivity of Biomaterials Measured with Self-Heated Thermistors," *International Journal of Thermodynamics*, 6(3):301-311, 1985.
Written Opinion, mailed Jun. 16, 2011, for PCT/US2010/050945, 4 pages.
Written Opinion, mailed Jan. 8, 2007, for PCT/CA2006/001123, 6 pages.
Written Opinion, mailed Sep. 4, 2009, for PCT/US2009/043612, 6 pages.
Gelbart et al., "Method and Device for Closing Holes in Tissue", Office Action mailed Nov. 20, 2014 for U.S. Appl. No. 13/652,299, 9 pages.
Goertzen et al., "Tissue Anchor System", Notice of Allowance mailed Dec. 3, 2014 for U.S. Appl. No. 13/247,380, 14 pgs.
Tegzes, "Medical Kit for Constricting Tissue or a Bodily Orifice, for Example, a Mitral Valve", Amendment filed Dec. 3, 2014 for U.S. Appl. No. 13/421,677, 17 pgs.
Dahlgren et al., "Medical Device, Kit and Method for Constricting Tissue or a Bodily Orifice, for Example, a Mitral Valve", Amendment filed Dec. 30, 2014 for U.S. Appl. No. 13/917,469, 18 pgs.
Lichtenstein et al., "System for Improving Diastolic Dysfunction", Office Action mailed Apr. 10, 2015 for U.S. Appl. No. 12/904,885, 67 pages.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Gelbart "Method and Device for Closing Holes in Tissue", Office Action mailed May 14, 2015 for U.S. Appl. No. 13/652,299, 67 pages.
Dahlgren et al., "Medical Device, Kit and Method for Constricting Tissue or a Bodily Orifice, for Example, a Mitral Valve", Amendment filed Jun. 4, 2015 for U.S. Appl. No. 13/917,469, 17 pgs.

\* cited by examiner

100; # METHOD FOR ANCHORING A MITRAL VALVE

BACKGROUND

1. Technical Field

The invention relates to minimally invasive cardiac surgery.

2. Description of the Related Art

The art of artificial heart valves is well known. Recently there is a strong interest in minimally invasive methods of replacing defective heart valves, and in particular in percutaneous deployment methods. In those procedures, the new valve is delivered and all the steps to install it, are performed via a fairly narrow catheter, typically 8-10 mm diameter.

Replacing major surgery with the small incision needed for inserting such a catheter is a major step in cardiac surgery.

The mitral valve is a particularly difficult case as the heart has an unfavorable geometry for anchoring a replacement valve. In conventional cardiac surgery the new valve is sutured to the tissue around the natural valve, which is surrounded by an annular ring of more rigid tissue known as the valve annulus. This procedure is not practical for percutaneous surgery. The main object of the invention is to devise an anchoring method for a replacement mitral valve. A further object is making the method both reversible and percutaneous.

BRIEF SUMMARY

An artificial mitral valve is anchored in the left atrium by placing the valve between the annulus of the natural mitral valve and an artificial annulus. The artificial annulus is formed by inserting a tool into the coronary sinus, and adjusting the tool to force the wall of the left atrium to form an annulus above the artificial valve, thus locking the artificial mitral valve in place and forming a hemostatic seal. The artificial mitral valve can be held by compression from above or by circumferential compression from the tool. The compression can be released in order to remove the artificial mitral valve, if desired.

DETAILED DESCRIPTION

Figure 1:
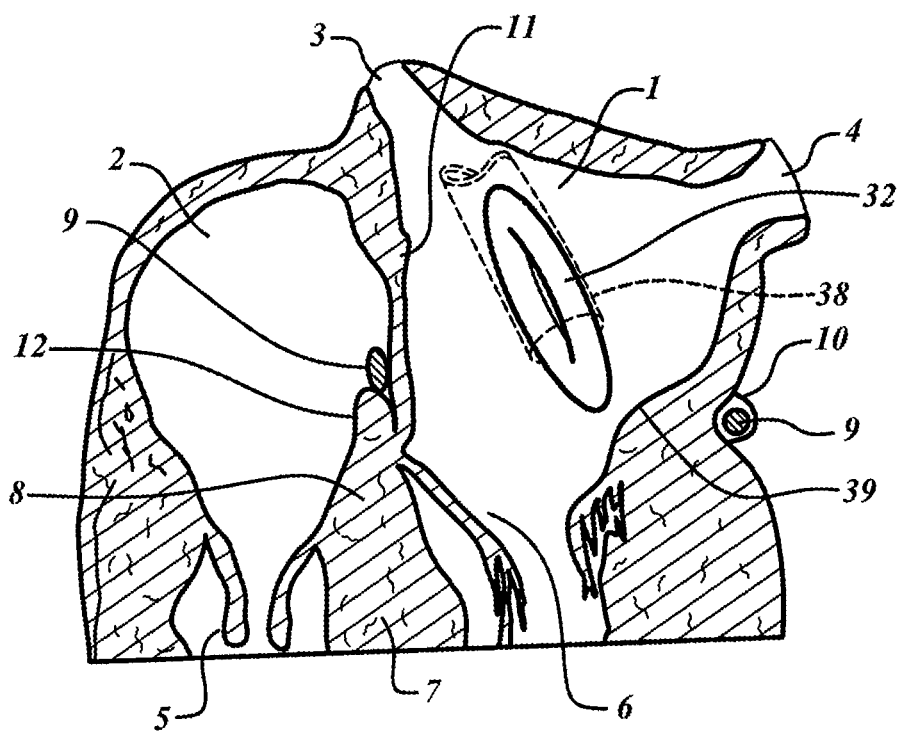
FIG. 1 is a longitudinal cross section of the heart, showing the left and right atriums.

Referring now to FIG. 1, the cross section of the upper part of the heart shows the left atrium 1, the right atrium 2, pulmonary veins 3 and 4, tricuspid valve 5 and mitral valve 6, interventricular septum 7, atrioventricular septum 8, coronary sinus 10, interatrial septum 11, and tendon of Todaro 12. An artificial mitral valve 32 is introduced into the left atrium to replace a defective mitral valve 6. The artificial mitral valve 32 is of flexible construction in order to be deployed percutaneously via a catheter 38. For deployment the artificial mitral valve 32 is compressed into an elongated oval shape. The art of percutaneous deployment is well known in minimally invasive surgery. One way to deploy the artificial mitral valve 32 is to pass catheter 38 via septum 11, after entering the right atrium via the superior vena cava. An anchoring tool 9 is shown in FIG. 1 already inside the coronary sinus 10. The periphery of mitral valves 6 is less flexible and forms a shape 39 known as the mitral valve annulus.

Figure 2:
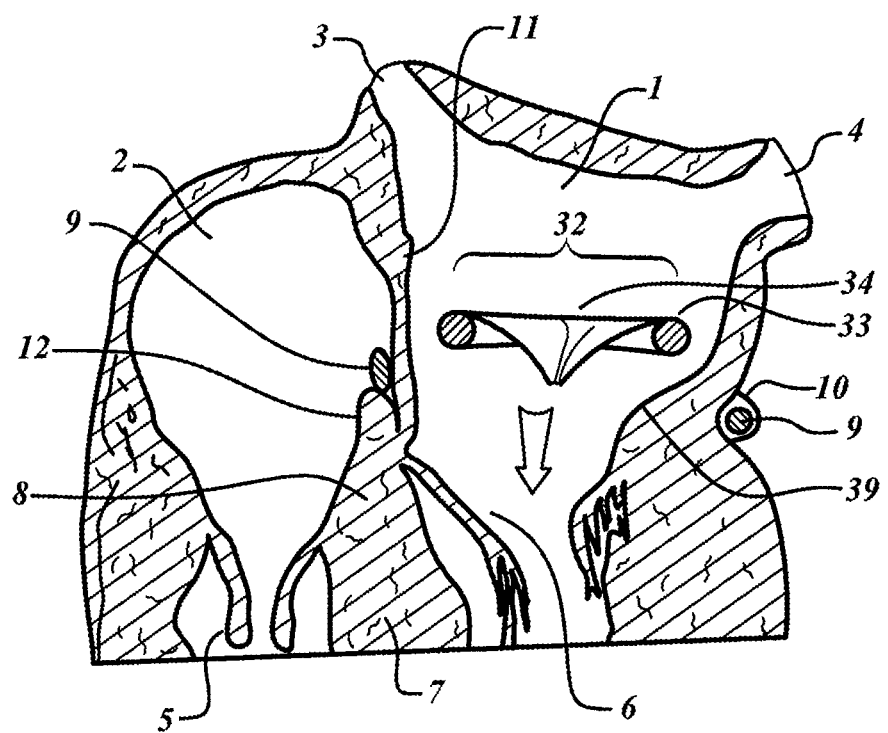
FIG. 2 is a longitudinal cross section of the heart as in FIG. 1, showing a deployed artificial mitral valve.

Referring now to FIG. 2, the artificial mitral valve 32 is allowed to expand to its normal form. The artificial mitral valve 32 comprises of very flexible leaflets 34, and a less flexible annulus 33. The overall shape of the artificial mitral valve 32 is matched to the area above the mitral valve annulus, which is generally "D" shaped. The cross section of the annulus can be round, oval, rectangular or any other shape suitable for forming a hemostatic seal when seated above the annulus 39 of the defective mitral valve 6. Annulus 33 can also be composed of multiple materials, some more rigid to better control the shape and some more flexible to help if forming a hemostatic seal. For example, annulus 33 can be made of soft silicone rubber with a Nitinol wire ring embedded in the annulus to control the shape of the ring. The leaflets 34 can be made of silicone rubber, Dacron or any other thin flexible material which is compatible with the heart. Artificial mitral valves capable of being delivered via a catheter are commercially available from Edwards Life Sciences (www.edwards.com).

At this stage the anchoring tool 9 is in the coronary sinus but the anchoring tool 9 is left in the relaxed and flexible position, as explained later on.

Figure 3:
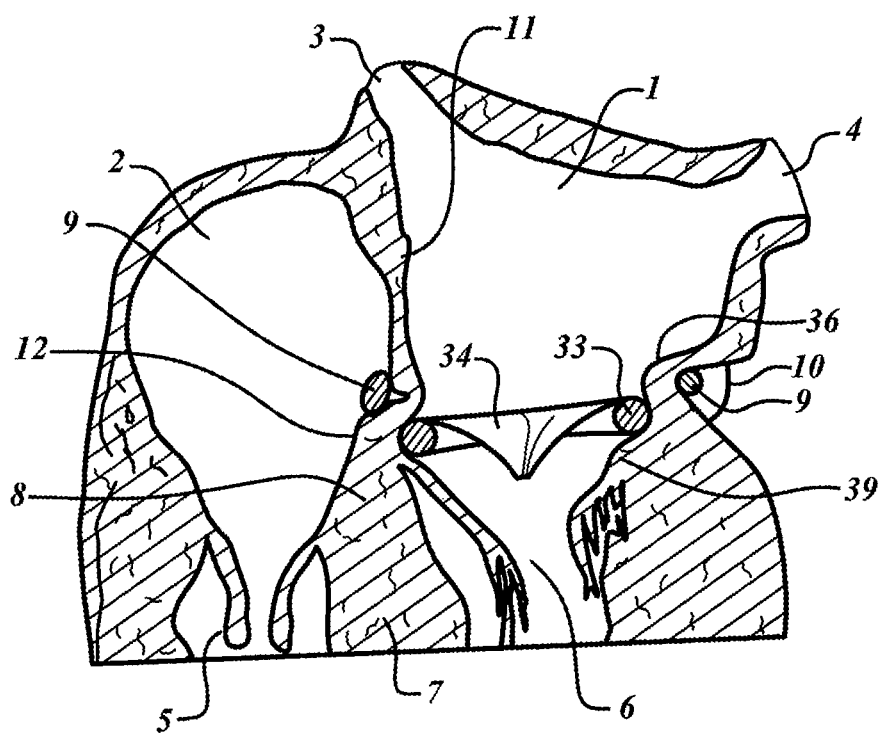
FIG. 3 is a longitudinal cross section of the heart as in FIG. 1, showing an artificial mitral valve anchored in place according to the invention.

After the artificial mitral valve 32 is placed at the final location above the defective valve 3, the artificial mitral valve 32 has to be anchored into place. The artificial mitral valve 32 is brought into the correct position by using the delivery catheter to push the artificial mitral valve 32 downwards (this is also aided by the downwards blood flow). To secure the artificial mitral valve 32 in place, a second annulus, similar to the natural annulus 39 of the mitral valve 6, is created above the artificial mitral valve 32 by a ring-like anchoring tool 9 shown in cross section in FIG. 3. When anchoring tool 9 is tightened it pulls in the outside wall of left atrium 1 as well as interatrial septum 11 to form an almost full ring 36 around the valve annulus 33. This locks the artificial mitral valve 32 between the natural annulus 39 of mitral valve 6 and an artificial annulus 36. By further tightening anchoring tool 9 a hemostatic seal is established. Since valve annulus 33 is flexible (as is anchoring tool 9) it will conform to the exact shape of the natural annulus 39. Inside the right atrium, tool 9 is placed against the interatrial septum 11 just above tendon of Todaro 12.

Figure 4:
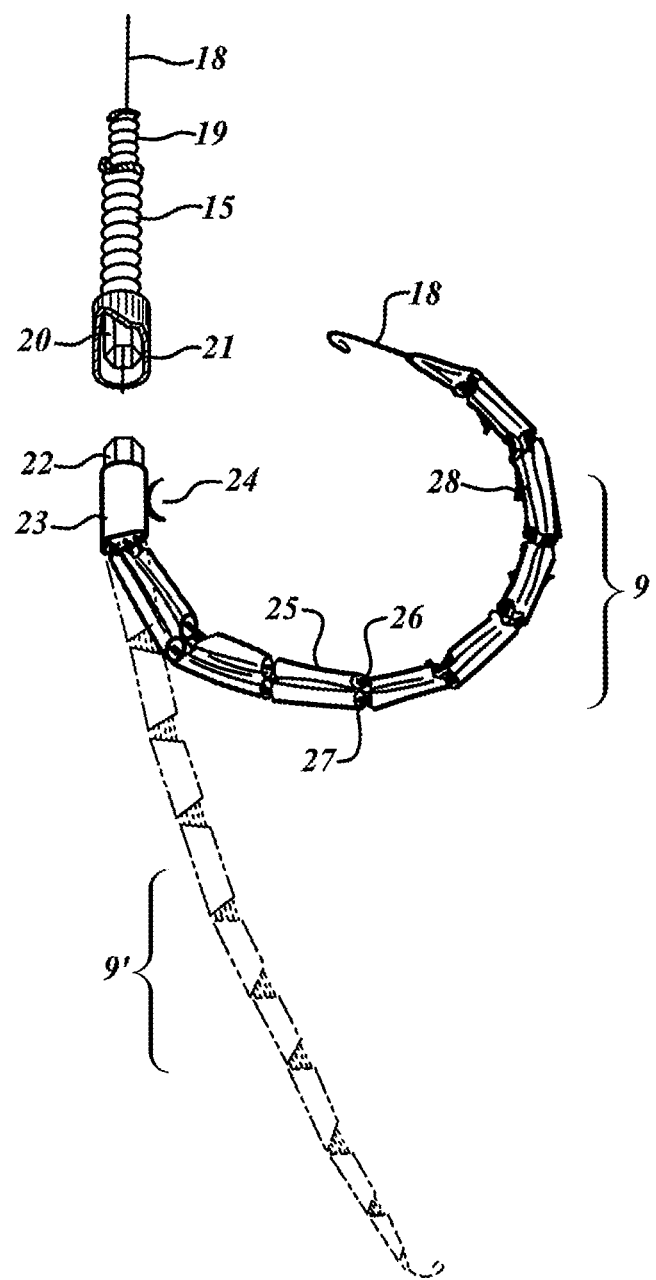
FIG. 4 is a general view of the anchoring tool.

Details of anchoring tool 9 are shown in FIG. 4. Anchoring tool 9 is made of rigid links 25 connected by two flexible cables 26 and 27. Protrusions or barbs 28 can be added to increase anchoring in the coronary sinus. A barb 24 is mounted on end piece 23. This barb is covered by tube 21 of adjustment tool 15. When tube 21 is detached from end piece 23, barb 24 springs open and secures the position of anchoring tool 9 relative to septum 11 (shown in FIG. 1). The shape of anchoring tool 9 is adjusted by tensioning cable 26 by turning screw 22 using matching socket 20 connected to inner flexible tube 19. Both anchoring tool 9 and flexible tube 15 have a hole for guide wire 18. Flexible tube 19 can rotate freely inside flexible adjustment tool 15. Both adjustment tool 15 and inner flexible tube are made of metal bellows type hose or of a braided hose, as these type hoses are torsionally stiff but easy to bend. It is desirable to make screw 22 and socket 20 of a ferromagnetic material, and provide a small rare-earth magnet (not shown) inside socket 20. This facilitates locating screw 22 if adjustment tool 15 has to be re-connected to anchoring tool 9 inside the heart.

Figure 5:
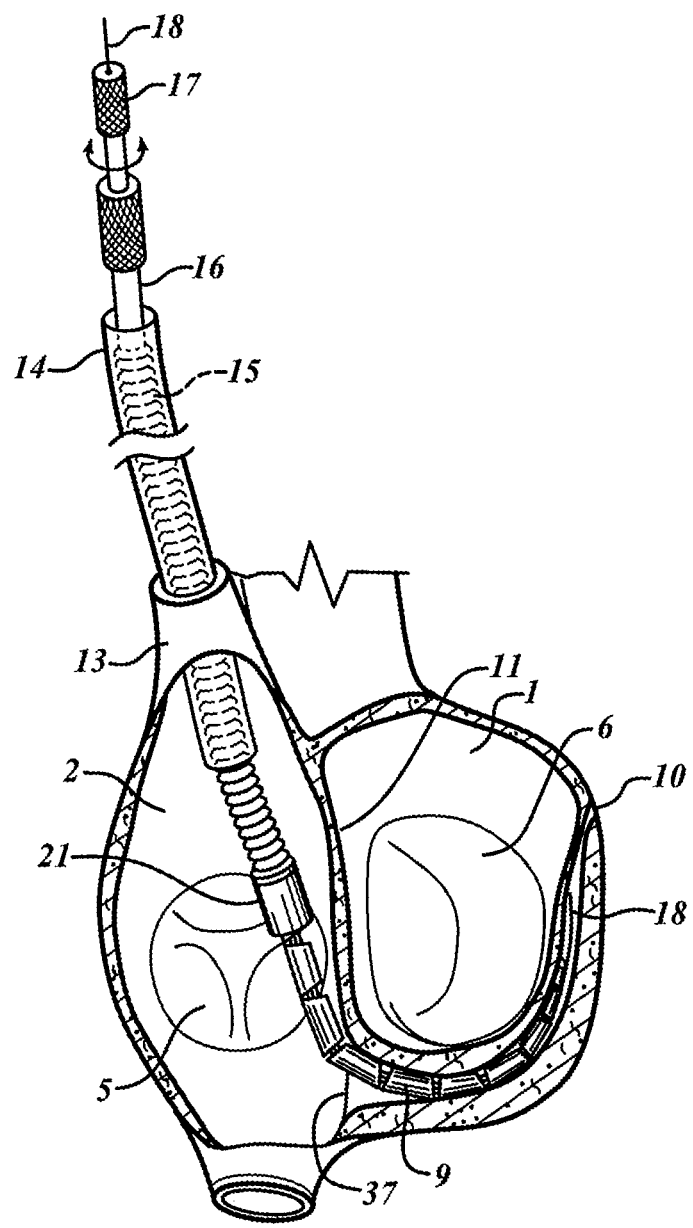
FIG. 5 is a schematic view showing the use of the anchoring tool in a percutaneous operation.

Referring now to FIG. 5 and FIG. 4, the percutaneous use of an embodiment of the invention is shown. Anchoring tool 9 is attached to flexible adjustment tool 15 and is inserted into the right atrium 2 via catheter 14, typically through the superior vena cava 13 over a guide wire 18. Guide wire 18 is inserted first, via ostium 37, all the way to the end of the coronary sinus 10. Tools 9 and 15 are guided by the wire 18. Anchoring tool 9 can be bent into shape by turning knob 17 while holding shaft 16. Turning knob 17 will turn socket 20 and tighten cable 26. To release adjustment tool 15, knob 17 is pressed into shaft 16 causing tool 9 to be ejected from tube 21 and embed barb 24 in septum 11. The operation is fully reversible as long as guide wire 18 is in place. It is even possible to re-adjust or remove anchoring tool 9 at a later date, if socket 20 can be lined up with screw 22. This is assisted by magnetic attraction, as explained earlier. The reversibility of the operation is a major advantage should the artificial mitral valve 32 need to be removed.

The same tool can be used both as an adjustment tool for controlling regurgitation in a natural mitral valve and as an anchoring tool for an artificial mitral valve. This is important as in many cases an adjustment can correct the problem in the natural mitral valve, without need for installing an artificial mitral valve. At a later date an artificial mitral valve may be required. In such a case, anchoring tool 9 simply needs to be loosened, an artificial mitral valve installed and anchoring tool 9 re-tightened.

Figure 6A:
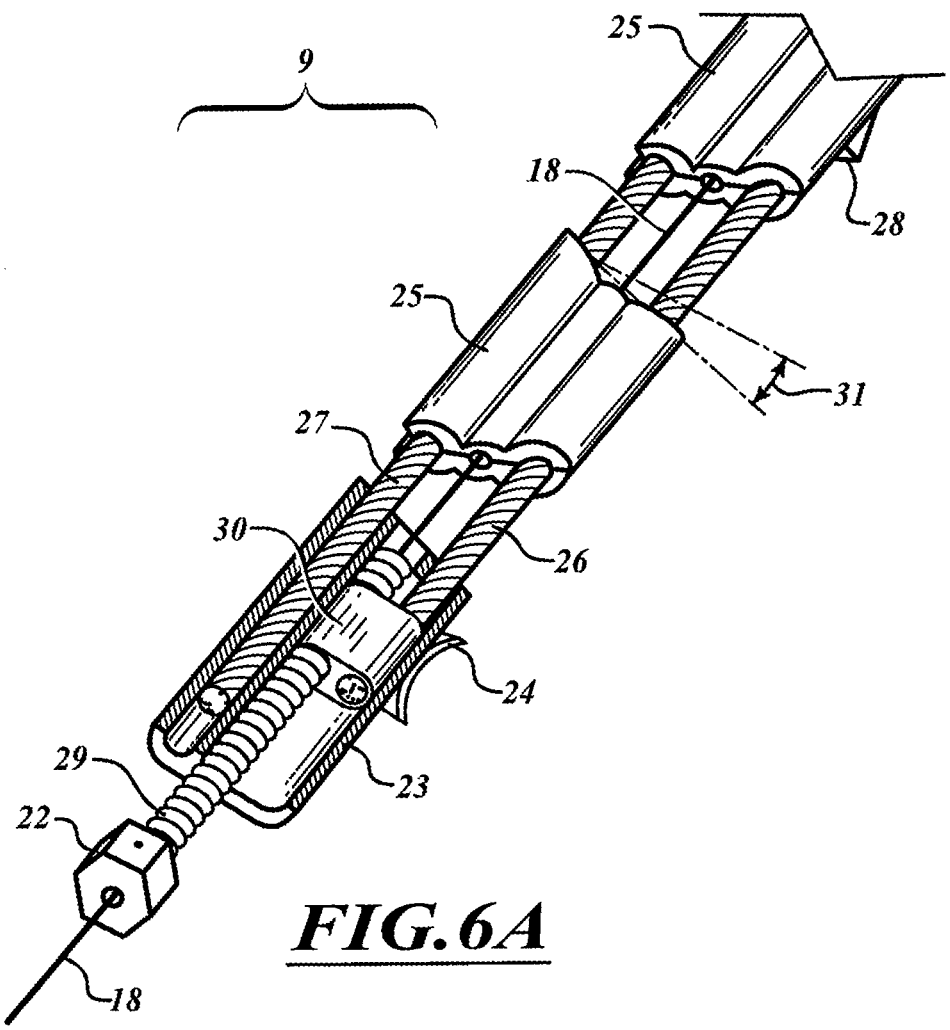
FIG. 6A is a partial isometric view of the anchoring tool.
Figure 6B:
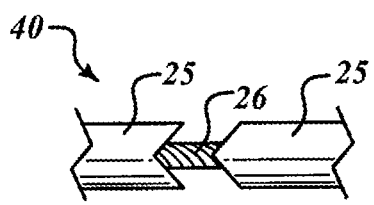
FIG. 6B is a side elevational view of a portion of the anchoring tool.

A more detailed view of anchoring tool 9 is given in FIGS. 6A and 6B. Each one of links 25 are cut at an angle 31. Angles 31 and length of links 25 determine the final shape of anchoring tool 9 when cable 26 is fully tightened. In order to keep links 25 in a single plane, the ends are cut in a V-shape as shown in insert drawing 40, which depicts a side view of links 25. The V shaped cut can be aligned with the longitudinal axis, as shown in 40, or can form an arbitrary angle to it. In such a case anchoring tool 9 will acquire a three-dimensional shape when tightened rather than fit in a single plane. Tightening screw 22 pulls nut 30 and tensions cable 26, causing anchoring tool 9 to tighten towards the final shape. The cross section of links 25 is designed to allow maximal blood flow in the coronary sinus. Cable 26 is permanently attached to nut 30 and to the last link (not shown), which is the link furthest away from end piece 23. Cable 27 is permanently attached to the last link but not attached to end piece 23 in order to accommodate the change in length when anchoring tool 9 is changing from straight to curved. When cable 26 is loosened, anchoring tool 9 is very flexible, similar to a chain. When cable 26 is fully tight, anchoring tool 9 can exert considerable force (a few Kg) in the radial direction.

By the way of example, anchoring tool 9 is made of type 316 stainless steel, with links 25 having a cross section of about 2×3 mm, and a length of about 12 mm each. Each links has three holes about 1 mm diameter each. Cables 26 and 27 are made of stainless steel as well and have an outside diameter of about 0.8 mm. Screw 22 is made of 400 series stainless (to be magnetic) and is 2 mm diameter with 3 mm hex head.

The term "annulus" in this disclosure has to be broadly interpreted. It need not be a complete circle, as anchoring tool 9 encircles the majority of the artificial mitral valve circumference but not all of it, due to the presence of the aortic valve. The term "artificial annulus" should be understood as any arc-like retention feature formed by anchoring tool 9. Also, while the preferred embodiment shows the artificial annulus formed above the artificial mitral valve, it is obvious that the artificial annulus can be used to anchor the artificial mitral valve even without being above it. By the way of example, the periphery of the artificial mitral valve can have a groove and the artificial annulus can engage this groove. In a different embodiment the base of the artificial mitral valve can be wider than the top part, thus allowing anchoring by an artificial annulus. It is also clear that the anchoring tool 9 need not be made of individual links. The anchoring tool 9 can be made of an elastic material such as Nitinol and rely on the elastic force to form the artificial annulus. While the term "anchoring" in this disclosure implies forming a hemostatic seal between the artificial valve annulus and the existing mitral valve annulus, it is understood that the seal need not be perfect to practice the invention, as any small gaps tend to seal themselves over time due to formation of scar tissue and deposits. A further improvement can be in the form of adding magnets to the artificial valve annulus and adding ferromagnetic material to anchoring tool 9. This helps align the artificial mitral valve 32 with the artificial annulus. While the force of the magnets may be insufficient to retain the artificial mitral valve 32, it is sufficient to hold in the correct position until anchoring tool 9 is tightened.

Figure 7:
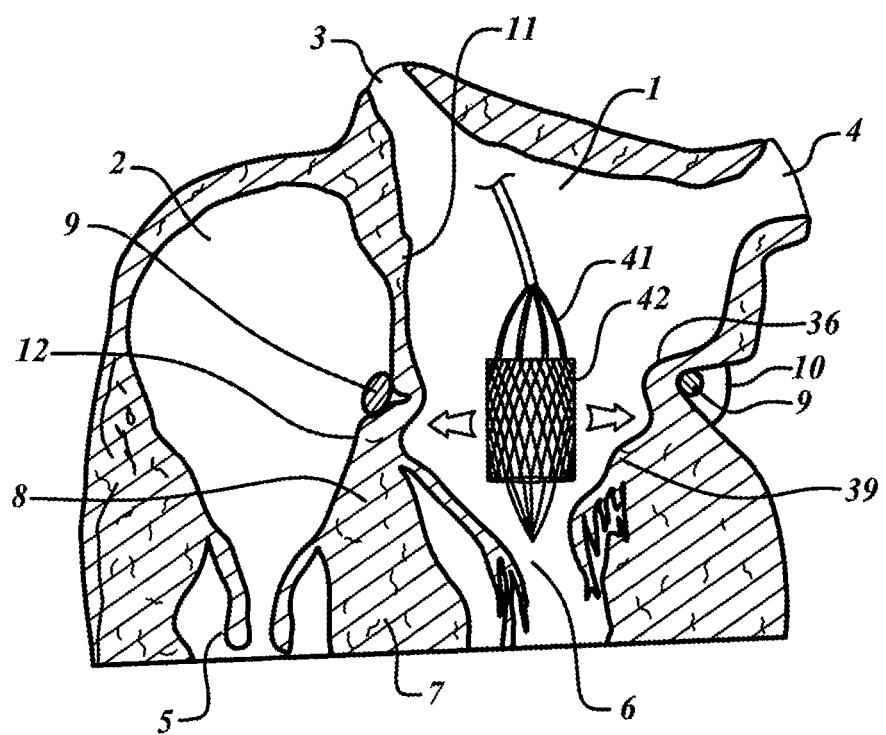
FIG. 7 is a schematic view showing the use of the invention in anchoring a balloon expandable valve.

An alternate way of using the artificial annulus is to use it as an anchoring base for a balloon expandable valve. Balloon expandable valves are well known in the art and are used, for example, as replacement aortic valves. Until now they were not used as mitral valves since there was no sufficiently rigid surface to expand the balloon against. FIG. 7 shows use of an anchoring tool 9 to form a rigid artificial annulus 36, then expansion of a balloon mounted valve 42, mounted on balloon 41, into the rigid structure that was formed.

The various embodiments described above can be combined to provide further embodiments. All of the commonly assigned US patent application publications, US patent applications, foreign patents, foreign patent applications and non-patent publications referred to in this specification and/or listed in the Application Data Sheet, including but not limited to U.S. nonprovisional patent application Ser. No. 13/872,870, filed Apr. 29, 2013, U.S. nonprovisional patent application Ser. No. 11/475,978, filed Jun. 28, 2006, issued as U.S. Pat. No. 8,449,605, are incorporated herein by reference, in their entirety.

The invention claimed is:

1. A device to anchor an artificial mitral valve via a coronary sinus of a heart, the coronary sinus which at least partially extends about a natural mitral valve of the heart, the artificial mitral valve being insertable inside an opening formed by the natural mitral valve in a left atrium of the heart to replicate a function of the natural mitral valve, the device comprising:

a terminal link comprising a guide wire bore sized and dimensioned to receive a guide wire therethrough, the guide wire configured to provide a path to the coronary sinus, and the guide wire bore comprising an entry point in a first portion of the terminal link and an exit point in a second portion of the terminal link different from the first portion;

a first cable comprising a first end, the first end of the first cable attached to the terminal link; and a series of non-terminal links each having a first end and a second end spaced apart from each other along a longitudinal axis and a first cable bore extending between the first end and the second end of the respective non-terminal link that receives the first cable therethrough, wherein a tension of the first cable is adjustable to transition the device between a flexible state wherein the series of non-terminal links are freely movable with respect to each other and a more rigid state wherein the series of non-terminal links are substantially fixed with respect to each other, the device being at least partially insertable into the coronary sinus in the flexible state such that the series of non-terminal links and the terminal link at least partially encircle a portion of the artificial mitral valve, and which device forms an artificial annulus in the more rigid state to physically secure the artificial mitral valve in the opening.

2. The device of claim 1, further comprising a tension adjustment coupler proximate a second end of the first cable opposite the first end of the first cable, wherein movement of the tension adjustment coupler in one direction increases the tension in the first cable and movement of the tension adjustment coupler in another direction decreases the tension in the first cable.

3. The device of claim 2 wherein the second portion of the terminal link is an end of the terminal link.

4. The device of claim 2 wherein the tension adjustment coupler comprises a nut and a tightening screw threadably coupled with the nut.

5. The device of claim 4 wherein the tightening screw comprises a guide wire bore sized and dimensioned to receive the guide wire therethrough.

6. The device of claim 1 wherein the series of non-terminal links each further comprises a guide wire bore sized and dimensioned to receive the guide wire therethrough.

7. The device of claim 1 wherein the first end of each of the non-terminal links comprises a first surface and the second end of each of the non-terminal links comprises a second surface, the first and the second surfaces being disposed in a configuration such that when the tension of the first cable is applied, the first surface of one of the non-terminal links abuts the second surface of an adjacent one of the non-terminal links to selectively fix the non-terminal links in a predetermined orientation.

8. The device of claim 7 wherein the first surface and the second surface of each of the non-terminal links are positioned at an oblique angle relative to the respective longitudinal axis such that the longitudinal axes of adjacent non-terminal links are non-parallel when the device is in the more rigid state.

9. The device of claim 7 wherein the first surface and the second surface of each of the non-terminal links are positioned such that the non-terminal links fit in a single plane when the device is in the more rigid state.

10. The device of claim 7 wherein the first surface of at least one subset of the non-terminal links comprises a first alignment profile and the second surface of the at least one subset of the non-terminal links comprises a second alignment profile complementary to the first alignment profile such that, when the device is in the more rigid state, the first and the second alignment profiles of adjacent non-terminal links join together to maintain alignment of adjacent links at a predetermined orientation.

11. The device of claim 7 wherein the first surface and the second surface of each of the non-terminal links are positioned such that the non-terminal links acquire a non-single plane, three-dimensional shape when the device is in the more rigid state.

12. The device of claim 1, further comprising a second cable, the series of non-terminal links each having a second cable bore extending between the first end and the second end of the respective non-terminal link that receives the second cable therethrough, a first end of the second cable being attached to the terminal link.

13. The device of claim 12, further comprising a tension adjustment coupler attached to a second end of the first cable opposite the first end of the first cable, wherein movement of the tension adjustment coupler in one direction increases the tension in the first cable and movement of the tension adjustment coupler in another direction decreases the tension in the first cable, the second cable comprising a second end opposite the first end of the second cable, the second end of the second cable being free from attachment to the tension adjustment coupler.

14. The device of claim 13 wherein the tension adjustment coupler comprises a nut and a screw threadably coupled with the nut, the screw comprising a ferromagnetic material.

15. The device of claim 1 wherein the terminal link is arranged to be inserted into the coronary sinus ahead of the series of non-terminal links.

16. A device to anchor an artificial mitral valve via a coronary sinus of a heart, the coronary sinus which at least partially extends about a natural mitral valve of the heart, the artificial mitral valve being insertable inside an opening formed by the natural mitral valve in a left atrium of the heart to replicate a function of the natural mitral valve, the device comprising:

a terminal link configured to be inserted furthermost into the coronary sinus, the terminal link comprising a guide wire bore sized and dimensioned to receive a guide wire therethrough, the guide wire bore comprising an entry point in a first portion of the terminal link and an exit point in a second portion of the terminal link different from the first portion; and a series of non-terminal links each having a first end and a second end spaced apart from each other along a longitudinal axis, wherein the device having a flexible state wherein the series of non-terminal links are freely movable with respect to each other and a more rigid state wherein the series of non-terminal links are substantially fixed with respect to each other, the device being at least partially insertable into the coronary sinus in the flexible state such that the series of non-terminal links and the terminal link at least partially encircle a portion of the artificial mitral valve, and which device forms an artificial annulus in the more rigid state to physically secure the artificial mitral valve in the opening.

\* \* \* \* \*